(12) United States Patent
Simon et al.

(10) Patent No.: US 9,207,294 B1
(45) Date of Patent: Dec. 8, 2015

(54) METHOD AND APPARATUS FOR THE CONTACTLESS DETERMINATION OF ELECTRICAL QUANTITIES

(76) Inventors: Sven Simon, Stuttgart (DE); Jürgen Hillebrand, Stuttgart (DE)

( * ) Notice: Subject to any disclaimer, the term of this patent is extended or adjusted under 35 U.S.C. 154(b) by 599 days.

(21) Appl. No.: 13/360,663

(22) Filed: Jan. 28, 2012

Related U.S. Application Data

(60) Provisional application No. 61/437,682, filed on Jan. 30, 2011.

(51) Int. Cl.
| | |
|---|---|
| *G01R 15/00* | (2006.01) |
| *G06F 19/00* | (2011.01) |
| *G01R 33/12* | (2006.01) |
| *H01L 21/02* | (2006.01) |
| *G01N 27/22* | (2006.01) |

(52) U.S. Cl.
CPC .......... *G01R 33/1238* (2013.01); *G01N 27/221* (2013.01); *H01L 21/02428* (2013.01)

(58) Field of Classification Search
CPC ......... G01F 1/662; G01F 1/74; G01N 27/221; H01Q 15/0046; H01Q 15/0086; G01R 33/1238; H01L 21/02428; G01Q 60/22; Y10S 505/887

USPC .............. 702/8, 28, 40, 49, 57, 159, 189; 324/663; 382/131; 250/393; 73/105
See application file for complete search history.

(56) References Cited

U.S. PATENT DOCUMENTS

| | | | | |
|---|---|---|---|---|
| 5,610,833 | A  * | 3/1997 | Chang et al. | 716/115 |
| 6,173,604 | B1 * | 1/2001 | Xiang et al. | 73/105 |
| 8,290,230 | B2 * | 10/2012 | Chen et al. | 382/131 |
| 8,618,817 | B2 * | 12/2013 | Jakoby et al. | 324/663 |

\* cited by examiner

*Primary Examiner* — John H Le
(74) *Attorney, Agent, or Firm* — Paul B. Heynssens Attorney at Law PLC

(57) ABSTRACT

Contactless determination of electrical parameters. The examples describe a method and apparatus for determining electrical parameters of assemblies (printed circuit boards and as well as passive components) by the contactless determination of the spatial distribution of material. The spatial distribution of material (two-dimensional or three dimensional), is determined for example by measurement by radiographic technology with an X-ray machine or a computer tomography or by an optical instrument. The electrical parameter is determined in each volume element whose size is determined by the resolution of the method used for determining the material distribution, or a partial structure of the conductive structure.

20 Claims, 3 Drawing Sheets

METHOD AND APPARATUS FOR THE CONTACTLESS DETERMINATION OF ELECTRICAL QUANTITIES

CROSS-REFERENCE TO RELATED APPLICATION

This application claims the benefit of U.S. Provisional Patent Application No. 61/437,682 filed Jan. 30, 2011, the contents of which are hereby incorporated by reference.

TECHNICAL FIELD

The invention relates to a method and apparatus for the contactless determination of electrical parameters by determining the distribution of material in a conductive structure.

BACKGROUND

Electrical parameters of conductive structures contained in printed wiring boards, packages or integrated circuits are determined with suitable electrical measuring instruments like Vector Network Analyzers, Spectrum Analyzers, TDR instrumentation or oscilloscopes. The disadvantage of these electrical measuring instruments, particularly at high frequencies e.g. in the GHz range can be the measurement uncertainty in general and the influence of the contact or the probe of the measurement instrument on the measurement result. Furthermore, no partial conductive structures of the assemblies can be measured contactless with the above mentioned electrical measuring instruments. With the method and apparatus described below these technical problems tend to be solved.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

The present example provides methods and apparatus for determining electrical parameters of a conductive structures based upon the contactless determination of the spatial distribution of the material.

The example relates to a method and apparatus for determining electrical parameters of assemblies (printed circuit boards, wires, cables, connectors and their spatial structures as well as passive components) by the contactless determination of the spatial distribution of material. The spatial distribution of material (two-dimensional or three dimensional), is determined by measurements made by an X-ray machine, a computed tomography apparatus, an optical measurement instrument, or a combination of these measurement instruments. The electrical parameter can be determined in each volume element whose size can be determined by the resolution of the method used for determining the material distribution, or a partial structure of the conductive structure. One embodiment of the invention relates to a method for determining electrical parameters. According to the invention at least one electrical parameter based on the material distribution of the considered object is determined by a X-ray machine, a computed tomography apparatus or an optical measurement instrument or a combination of these measurement instruments and is based on the so determined spatial distribution of material for calculating an electrical parameter to be determined.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

Figure 1:
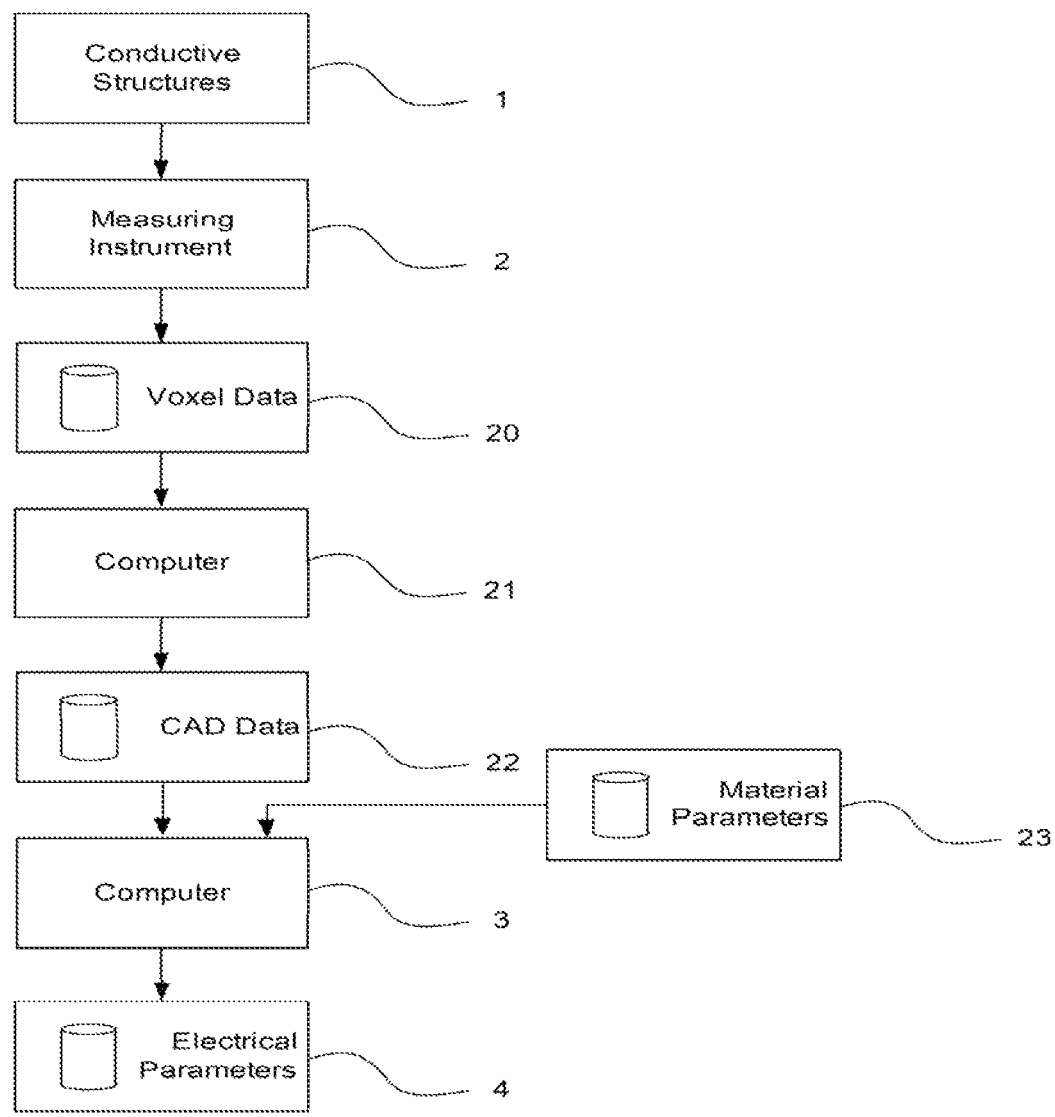
FIG. 1 shows an example of a device with a measuring instrument for determining the distribution of material and including a computer to determine the electrical parameters of a conductive structure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The examples below describe a contactless way of determining electrical parameters of a conductive structure, typically without direct coupling to the conductive structure. Although the present examples are described and illustrated herein as being implemented in an electrical system, the system described is provided as an example and not a limitation. As those skilled in the art will appreciate, the present examples are suitable for application in a variety of different types of modeled systems. The contactless determination of electrical parameters is further described in: Juergen Hillebrand, Marek Wroblewski, Sven Simon, "3D Computed Tomography for High-Speed Interconnect Characterization," in Conf. Proc., DesignCon 2011, Santa Clara, Calif., USA 2011; Juergen Hillebrand, Steffen Kieβ, Yu Wang, Marek Wroblewski and Sven Simon, "CAD Model Reconstruction of Solder Balls for the Computationally Efficient Electromagnetic Field Simulation," in Conf. Proc. IEEE 20th Conference on Electrical Performance of Electronic Packaging and Systems (EPEPS), pp. 279-282, October 2011; and Juergen Hillebrand, Steffen Kieβ, Marek Wróblewski and Sven Simon, "S-Parameter Extraction of Passive Sub-Circuits Using Computed Tomography Scans and Measured Substrate Material Parameters", in Proc. of 78th ARFTG Microwave Measurement Conference, Tempe, Ariz., USA, pp. 41-46, December 2011, the contents of which are incorporated herein by reference.

One aspect of the example described below is to determine the material distribution of a conductive structure and to compute the electrical parameters instead of applying a direct electrical measurement method, such as one that makes direct contact with the conductive structure. The material distribution can be determined in 3-dimensions or 2-dimensions. In the 2-dimensional case the value of the 3rd dimension can be assumed to be known, such that the 3-dimensional material distribution is given. The conductive structures of which an electrical parameter can be determined may consist of transmission lines, wires, components such as inductors or capacitors or interconnecting lines of a particular exemplary spatial structure, as well as passive devices. Such conductive structures can be contained in PCBs, IC packages, cables, connectors and or the like. The two- or three-dimensional material structure can be measured by x-ray technology, computed tomography, or optical measurement instruments or a combination of these measurement instruments or methods. In particular, the CT scanner employed for the determination of a 3-dimensional structure of a material may be suitable. This allows determination of the material for the full set of volume elements of the considered object. As it is known to those skilled in the art, and may be assumed here, that for each material to be measured, in the conductive structure, the specific electrical properties such as the resistivity or the dielectric constant are known. Thus for each volume element, its electrical properties can be assigned based on the identification of the material by means of an x-ray apparatus, computed tomography apparatus or an optical measurement instrument or a combination of these measurement instruments.

Electrical parameters, or parameters, of the conductive structure can be, for example S-parameters, admittance-parameters (Y-parameters), impedance parameters (Z-parameters), impedance or conductance profile of a line, capacitance of a cable, or the like. Furthermore, the electrical equivalent circuits of conductive structures such as a complex line structure (e.g. consisting of layer changes with vias or electrical loads based on IC packages) can be used in the form of a netlist derived by the proposed method for further use in simulation and design tools.

One example of the invention relates to a method for determining electrical parameters, where the material distribution of a conductive structure from which at least one electrical parameter will be determined by radiographic technology or computed tomography or by using an optical measurement instrument and the spatial distribution of the material distribution for calculating an electrical parameter is determined.

An electrical parameter can be determined from the distribution of material, either by use of formulas and tables, or by the numerical calculation e.g. computing the electric and magnetic fields based on an excitation of the electric or magnetic field around this conductive structure.

The method provided can identify at least one partial structure of the assembly with a position-dependent permittivity and permeability based on the specific spatial distribution of the material. Furthermore, surface properties for determining the electrical parameters can be taken into account.

The distribution of material measured by the above mentioned radiographic techniques can be compared with a material distribution that is based on the CAD data to fabricate the conductive structure to determine the acceptable geometric tolerances of the CAD model based on the specified electrical tolerances. Furthermore, electrical equivalent circuits of the conductive structure can be determined.

The conductive structure can be reproduced based on the determined electrical values. The method can also be used for reproduction of a conductive structure with the same electrical properties of an original conductive structure.

Another alternative example relates to a device for determining electrical parameters based on a radiographic element, a x-ray apparatus, a computed tomography apparatus, or an optical measurement instrument (including optical microscopy), to determine the material distribution of a conductive structure, from which at least one electrical parameter is determined, and by calculating an electrical parameter based on the spatial distribution of material.

The method of calculation may further be configured to execute a method according to the invention and as explained above. Further advantages and applications of the present invention will become apparent from the following description in connection with the embodiments shown in the drawings.

Figure 2:
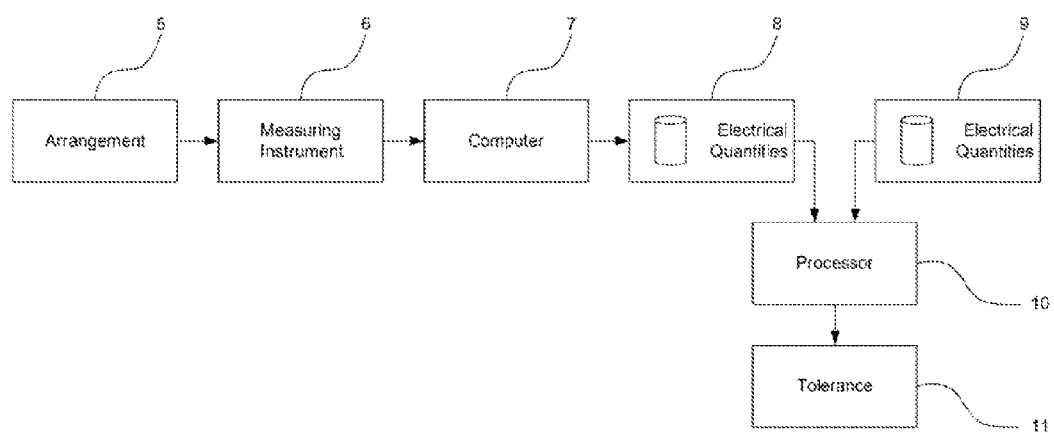
FIG. 2 shows the comparison of the specified electrical parameters (nominal values) of the present example with the electrical parameters on the basis of the CAD data used to produce or specify the conductive structure.
Figure 3:
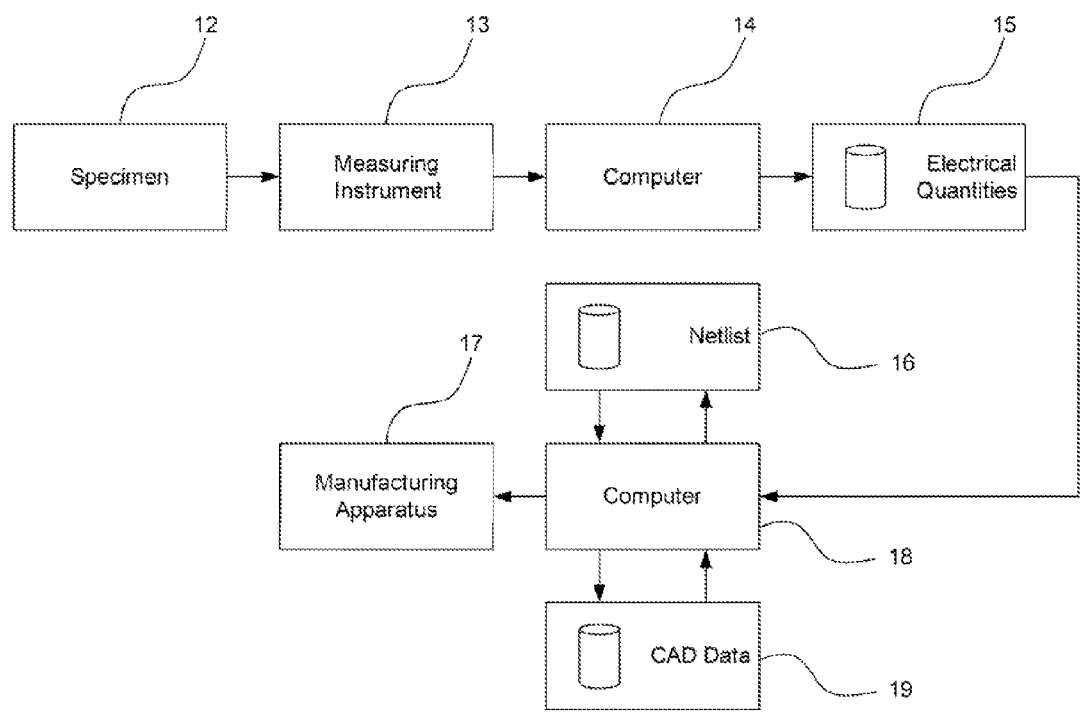
FIG. 3 shows an example of a device for reproduction of a conductive structure with substantially the same electrical properties as compared to an original conductive structure of the example.

The drawings show in FIG. 1 an example of a device with a measuring instrument for the distribution of material and a computer to determine the electrical parameters of a conductive structure according to the invention;

FIG. 2 the comparison of the specified electrical parameters (nominal values) of the present example with the electrical parameters on the basis of the CAD data used to produce or specify the conductive structure according to the invention; and FIG. 3 an example of a device for reproduction of a conductive structure with the same electrical properties as compared to an original structure of the invention;

In FIG. 1, a device for determining the values of an electrical variable according to the invention is shown. To determine the values of the electrical parameters that are stored in the memory 4, the conductive structure 1 is analyzed, for example a circuit board with electronic components, with the measuring instrument 2, which measures the distribution of material throughout the conductive structure 1. The measurement instrument in the considered case, is a computed tomography scanner, but can also be an X-ray apparatus or an optical measurement instrument or a combination of those.

The data determined by the CT scan are called voxels to which a location-dependent damping or energy difference of the received X-ray radiation compared to the transmitted X-ray radiation of the CT scanner can be assigned on the basis of the measurement. From this 3-dimensional set of voxel data, the three-dimensional material distribution is determined by the appropriately equipped computer 21 by identifying the material type like a conductor material or dielectric material of each voxel value of each voxel. With this three-dimensional distribution of material which is considered as CAD data 22 which can be used to fabricate the conductive structure by the computer 3 with analytical formulas and numerical method determines the electrical parameters, which are then stored in the memory 4. This requires the electrical parameters 23 of the material. For example, the impedance of a transmission line can be determined with analytical formulas based on a at certain line geometry. Alternatively, the electromagnetic fields are determined by simulation, by which the desired electrical parameters such as the impedance or s-parameters can be calculated. Computer 3 and computer 21 can be the same apparatus running different but associated software.

In order to determine the electrical parameters based on the material distribution the following method using the simulation of electromagnetic fields on computer 3 can be applied as an example:

1. Identify the material based on the voxel data value, e.g. gray level of a CT voxel or gray value of an X-ray image pixel. This can be done by a threshold with respect to the gray levels to distinguish between conductor material like metal and dielectric material. The material distribution obtained from the voxel data values are defined as CAD data 22 from now on. These CAD data could be imported in CAD tools for further processing. The voxel based representation used for the CAD data can be transferred to a polygon based representation of the same approximately the same spatial material distribution in order to reduce the amount of memory to store the CAD data.

2. The electrical properties of the different materials like dielectric constant of the dielectric material or the conductivity of the conductor material of the considered conductive structure has to be known and is used in addition to the CAD data 22 to calculate the electrical parameter of the conductive structure in the next step. The CAD data identifying the spatial distribution of conductor material and dielectric material plus the electrical properties of the material are imported into an EM field computations tool like CST (Computer Simulation Technology AG, with offices located at Bad Nauheimer Str. 19, 64289 Darmstadt, Germany,), HFSS (ANSYS HFSS software by ANSYS, Inc. with offices at Southpointe, 275 Technology Drive, Canonsburg, Pa. 15317), or the like. The electrical properties of the different materials can be determined by using a priori knowledge from physics or electrical engineering literature or the electrical properties of the used materials can measured. This measurement can be done independently of the investigated conductive structure such that simplified measurements can take place.

3. In this step the electrical parameters are computed. As an example, the scattering parameters $S_{mn}$ can be determined with the results from a finite-difference time-domain (FDTD) simulation (an exemplary treatment of this type of calculation may be found in: A. Elsherbeni and V. Demir, "The Finite-Difference Time-Domain Method for Electromagnetics with MATLAB® Simulations", SciTech Publishing, Inc., ISBN 978-1-891121-71-5, pp. 169-185, 2009) as follows:

$$S_{mn} = \frac{b_m}{a_n}. \tag{1}$$

Equation 1 expresses the scattering parameter $S_{mn}$ as a ratio of the incident and reflected power waves $a_n$ and $b_m$ associated with port m and n with the assumption that only port n is excited and all other ports are matched. Based on the power waves concept (an exemplary treatment of this type of calculation may be found in: K. Kurokawa, "Power Waves and the Scattering Matrix", IEEE Transactions on Microwave Theory and Techniques, vol. 13, no. 2, pp. 194-202, 1965) the power waves $a_n$ and $b_m$ are defined as $$a_n = \frac{V_n + Z_n I_n}{2\sqrt{|Re(Z_n)|}}, \quad b_m = \frac{V_m - Z_m^* I_m}{2\sqrt{|Re\{Z_m\}|}}, \tag{2}$$

where $V_n$, $V_m$, $I_n$ and $I_m$ are the voltages and currents at port n and ports m, which can be computed by using Equation 3 and 4 (an exemplary treatment of this type of calculation may be found in: A. Taflove and S. C. Hagnes, "Computational Electrodynamics: The Finite-Difference Time-Domain Method", Second Edition, Artech House, ISBN: 1-58053-076-1, pp. 703-765, 2000.) where the indices m and n are labeled as i. $Z_n$ and $Z_m$ are the impedances of the associated ports n and m.

$$V_i(t, x_i) = \int_{C_v} \vec{E}(t, x_i) \cdot d\vec{l}, \tag{3}$$

$$I_i(t, x_i) = \oint_{C_I} \vec{H}(t, x_i) \cdot d\vec{l}. \tag{4}$$

In Equation 3, $C_v$ is a contour extending from a defined voltage reference point (e.g. a ground plane) to the circuit at location $x_i$ (e.g. a metallic strip line or microstrip line that propagates the dominant transverse electromagnetic (TEM) mode). The contour $C_I$ in Equation 4 wraps completely around the conductor at its surface in the transverse plane.

FIG. 2 shows a device for comparing the electrical parameters determined by the measurement instrument with the electrical parameters that were used on the basis of CAD data to produce the conductive structure. The CAD data specify the material distribution of the produced conductive structure. With the measurement instrument like a computed tomography apparatus 6, the material distribution of the assembly 5 is measured. By the computer 7, the electrical parameters from the measured distribution of material is calculated and stored in the memory 8. The deviation in the spatial distribution leads to the deviation of the electrical parameters with respect to their nominal value. This tolerance-determination can be used as quality measure in a fabrication process.

The electrical parameters that were determined on the basis of the CAD data to generate the assembly 5, are located in the memory 9 and to compare measured values of electrical parameters in the memory 8. The determination of the electrical parameters located in the memory 8 is based on the illustration and described in principle of FIG. 1. The elements 5, 6, 7 and 8 in FIG. 2 are identical to the representations 1, 2, 3 and 4 of FIG. 1. The comparison of the data is done using the computer 10, which determines the respective tolerances of 11 between the CAD model and the determined parameters.

FIG. 3 shows a device for reproduction of a conductive structure with the same electrical properties as compared to the original is shown. The original can be reconstructed while maintaining the electrical properties. This does not necessarily mean the reproduction while maintaining the geometry. Changes such as the dielectric constant of the PCB material at a reproduction of the printed circuit board combined with another line width are chosen to ensure the same impedance characteristics of the reproduced printed circuit board. If only the line width of a line of a PCB has to be measured, simple X-ray technology instead of computed tomography or an optical measurement to measure the line width can be used. Furthermore, the roughness of the material can be measured and included in the electric models. One possibility is to measure the surface topography with a white light interferometer and a subsequent calculation of the roughness based on the surface data which has an influence on the computed electrical parameters. For example, the surface roughness increases the line resistance.

The principle of reproduction is shown in FIG. 3. The representation of blocks 12, 13, 14 and 15 corresponds to the blocks 1, 2, 3 and 4 of FIG. 1. The collected data contained in memory 15 are used to generate a netlist 16, which contains the electric model for the entire conductive structure. The generation of the netlist is done with computer 18. From this netlist, the CAD data 19 are determined for the manufacturing of a reproduced conductive structure in the production unit 17. The computer also handles the transmission of data or the direct control of the production unit 17.

The present invention enables the contactless determination of electrical parameters of conductive structures contained in circuit boards, packages, wires, connectors or integrated circuits and is therefore particularly suitable for the determination of electrical parameters of high frequency electronics because there are no repercussions due to sampling contacts which can distort the measurement.

Those skilled in the art will realize that the process sequences described above may be equivalently performed in any order to achieve a desired result. Also, sub-processes may typically be omitted as desired without taking away from the overall functionality of the processes described above.

The invention claimed is:

1. A method for determining electrical parameters, comprising: determining a material distribution of a conductive structure, by a non-contacting measurement apparatus to measure a spatial arrangement of at least one material making up the conductive structure; and
   determining electrical parameters of the conductive structure by calculating at least one electrical parameter based upon the measured spatial arrangement of the at least one material and known electrical properties of the at least one material whereby the measured spatial arrangement of the conductive structure is divided into a plurality of elements, and where a material contained in each element of the plurality of elements is identified from a recorded image of the conductive structure, and electrical properties of the material are assigned to each element of the plurality of elements and the plurality of elements electrical properties so obtained are used to determine electrical parameters of the conductive structure.

2. The method for determining electrical parameters of claim 1 wherein, the non-contacting measurement apparatus is an X-ray machine.

3. The method for determining electrical parameters of claim 1 wherein, the non-contacting measurement apparatus is a computed tomography machine.

4. The method for determining electrical parameters of claim 1 wherein, the non-contacting measurement apparatus is an optical instrument.

5. The method for determining electrical parameters of claim 1, wherein the electrical parameter of the conductive structure is determined, either by use of formulas and tables, or by a numerical calculation of electric or magnetic fields.

6. The method for determining electrical parameters of claim 1 further comprising determining electrical properties of a partial structure of an examined conductive structure without any influence of the electrical parameters of those parts of the conductive structure being neighbors to the partial structure.

7. The method for determining electrical parameters of claim 1, wherein surface characteristics are utilized for determining the electrical parameters.

8. The method for determining electrical parameters of claim 1, wherein a specific spatial distribution of material determined by the non-contacting measurement is compared with the material distribution, which is based on computer aided design data for modeling of the assembly to an admissibility of geometric tolerances to analyze electrical tolerances based on specific electrical parameters.

9. The method for determining electrical parameters of claim 1 further comprising determining further electrical equivalent circuits of the conductive structure.

10. The method for determining electrical parameters of claim 1 wherein, the conductive structure can be reproduced by electrically identical sizes.

11. The method for determining electrical parameters of claim 1, further comprising reproduction of the conductive structure with the same electrical properties as a template layout.

12. The method for determining electrical parameters of claim 1 wherein, each of the plurality of elements is made up of two dimensional pixel data to describe the spatial arrangement in two dimensions.

13. The method for determining electrical parameters of claim 1 wherein, each of the plurality of elements is made up of three dimensional voxel data to describe the spatial arrangement in three dimensions.

14. An apparatus for determining electrical parameters comprising:
   a radiation element to illuminate a sample whose electrical parameters are to be measured, by processing an image of the illuminated sample;
   an optical measurement instrument, to record a material distribution of a conductive structure illuminated by the radiation element so that at least one electrical parameter is determined from analysis of an optical image produced; and
   a calculation means for calculating an electrical parameter using a specific spatial distribution of the material distribution of the conductive structure, identification of material in the material distribution, and known properties of the material identified to determine the electrical parameter.

15. The apparatus for determining electrical parameters of claim 14, wherein the calculation means further comprises:
   determining a material distribution of a conductive structure, of which at least one electrical parameter is determined by a non-contacting measurement; and
   determining a spatial distribution of the material for use in calculating an electrical parameter.

16. An apparatus for a contactless determination of electrical parameters of a conductive structure comprising:
   non-contacting measurement equipment for determining a material distribution of the conductive structure by creating a digitized image of the conductive structure; and
   a computer for computing electrical parameters of the material distribution by dividing the digitized image into voxels, identifying the material in the voxel based upon analysis of the digital image, and assigning known parameters of the identified material to the voxel for use in computing the electrical parameters.

17. The apparatus for the contactless determination of electrical parameters of a conductive structure of claim 16, wherein determining the material distribution is done in three dimensions.

18. The apparatus for the contactless determination of electrical parameters of a conductive structure of claim 16, wherein the material distribution is represented by a set of volume elements.

19. The apparatus for the contactless determination of electrical parameters of a conductive structure of claim 16, wherein the material distribution is determined using radiographic technology.

20. The apparatus for the contactless determination of electrical parameters of a conductive structure of claim 16, wherein electrical properties assigned to each element of the set of volume elements is based on identification of the material based on a radiographic scan of the material.

* * * * *